United States Patent [19]

Gutierrez et al.

[11] 4,273,935

[45] Jun. 16, 1981

[54] SALTS OF PROPENE 1,1,2,3-TETRACARBOXYLIC ACID

[75] Inventors: Eddie N. Gutierrez, Fort Lee; Vincent Lamberti, Upper Saddle River, both of N.J.

[73] Assignee: Lever Brothers Company, New York, N.Y.

[21] Appl. No.: 74,702

[22] Filed: Sep. 12, 1979

Related U.S. Application Data

[62] Division of Ser. No. 905,720, May 15, 1978, abandoned, which is a division of Ser. No. 642,850, Dec. 22, 1975, Pat. No. 4,123,458.

[51] Int. Cl.$^3$ ............................................. C07C 57/02
[52] U.S. Cl. .................................................... 562/595
[58] Field of Search ......................... 562/595; 560/190

[56] References Cited

U.S. PATENT DOCUMENTS 2,782,228   2/1957   Dazzi .

Primary Examiner—Jane S. Myers
Attorney, Agent, or Firm—James J. Farrell; Melvin H. Kurtz; Irving N. Feit

[57] ABSTRACT

Novel polyfunctional compounds and a novel process for their preparation are disclosed. These compounds may be converted into the acid or salt forms of cis and trans aconitic acids as well as into a racemic mixture of isocitric acid, alloisocitric acid and the lactones of isocitric acid and alloisocitric acid and their salts. All of the acid and salt forms produced are useful as metal sequestrants and/or detergent builders. The novel polyfunctional compounds can also be saponified to their corresponding alkali metal salts which, in turn, are also metal ion sequestering agents and detergent builders. The polyfunctional compounds are the reaction products obtained from the reaction of selected salts of monoalkyl esters of maleic acid with selected active hydrogen containing compounds.

2 Claims, No Drawings

SALTS OF PROPENE 1,1,2,3-TETRACARBOXYLIC ACID

This is a divisional application of Ser. No. 905,720 filed May 15, 1978, now abandoned, which is a divisional application of Ser. No. 642,850, filed Dec. 22, 1975, now U.S. Pat. No. 4,123,458.

This invention broadly relates to novel polyfunctional compounds and a process for their preparation. The novel compounds may be converted into cis and trans aconitic acid and into a racemic mixture of isocitric acid, alloisocitric acid and the lactones of isocitric and alloisocitric acid. These compounds may also be saponified to form alkali metal salts corresponding to the particular compound employed. These salts, in turn, are metal sequestering agents and/or detergent builders. In the preferred embodiments the polyfunctional compounds are converted into either cis and trans aconitic acid or into a racemic mixture of isocitric acid, alloisocitric acid and the lactones of isocitric acid and alloisocitric acid and cis and trans aconitic acid, are useful as food acidulants and metal ion sequestrants. The alkali metal, ammonium and substituted ammonium salts of isocitric acid, alloisocitric acid and cis and trans aconitic acid having utility both as metal ion sequestrants and detergent builders.

The reaction of active hydrogen compounds with unsaturated esters such as esters of maleic acid is known and is generally accomplished by means of the well known Michael reaction. This reaction is considered thoroughly in Chapter 3 of Volume 10 of the publication entitled "Organic Reactions" edited by Roger Adams et al and published in 1959 by John Wiley & Sons Inc. In its original sense, as described in the publication, this reaction involves the addition of a door moiety containing an alpha-hydrogen atom in a system

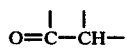

to a carbon-carbon double bond which forms part of a conjugated acceptor system of general formula

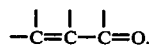

The addition proceeds under the influence of alkaline or basic catalysis.

Inherently in the Michael reaction, the donor moiety, under the influence of the basic catalysis (sodium metal is a catalyst of choice) forms an anion which in turn reacts with the beta carbon of the acceptor system. Through the use of this reaction a series of compounds have been prepared. A listing of a large number of these reactions and reaction products appears on pages 271-544 of the above-mentioned publication. The reaction in certain selected instances does not require an added catalyst because one of the reactants contains its own basic function. The Michael reaction, thus, is extremely useful for the synthesis of selected compounds. However, disadvantages arise in attempting to prepare certain mixed esters by this route because of transesterification which can take place under the conditions of the Michael reaction thereby producing mixtures of mixed esters in correspondingly diminished yield rather than a single mixed ester in relatively high yield. Further, reverse Michael reactions can occur to produce rearranged starting reactants. The resulting mixtures are normally extremely difficult to separate. These difficulties, thus, militate strongly against the use of the Michael reaction and indeed the applicability of this reaction for desired mixed ester products. In particular, with reference to the preferred preparations of aconitic acid and the mixture of isocitric acid, alloisocitric acid and their lactones in this invention, prior art processes were practically limited to natural fermentation. Although some synthetic methods have been proposed in the literature such as in the articles by Michael, J. pr. Chem. 49 (ii), 21 (1894), Pucher and Vickery, J. Biol. Chem. 163 169-184 (1946) and Gawron et al., J.A.C.S. 80 5856-5860 (1958), none of these methods appear to have been commercialized.

Accordingly, an object of the present invention is to provide a process for producing novel mixed ester compounds by adding an active methylene or an active methine compound across the double bond of selected salts of maleic acid esters, wherein the reverse Michael reaction is substantially inhibited and wherein the reaction takes place in the absence of added alkaline catalyst.

A further object is to produce a novel polyfunctional compound which may be converted into cis and trans aconitic acid or into a mixture of isocitric acid, alloisocitric acid and the lactones of isocitric acid and alloisocitric acid as well as salts of these acids.

Yet another object is to provide a novel method for preparing novel polyfunctional compounds which can be converted into metal ion sequestrants and detergent builders.

Other objects and advantages will appear as the description proceeds.

The attainment of the above objects is made possible by this invention which includes novel polyfunctional compounds as well as a process for their preparation. These novel compounds have the general formula (I) as follows:

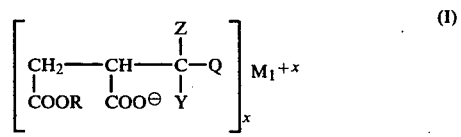

wherein R is a primary alkyl group of one to four carbon atoms and preferably a methyl or ethyl group, wherein $M_1$ is hydrogen, calcium, magnesium, strontium, barium, sodium, potassium or lithium, wherein x is 1 or 2 and is equivalent to the valency of $M_1$, wherein O is preferably H but in alternative embodiments may also represent a primary alkyl group of 1 to 4 carbon atoms wherein Z is phenyl; substituted phenyl having electron withdrawing substituents on the ring such as, for example, chlorine, bromine and nitro; cyano (—CN);

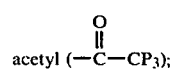

nitro (—NO$_2$) or a carboxylic ester (—COOR$_2$) wherein R$_2$ is a primary alkyl group containing 1 to 4 carbon atoms, preferably a methyl or ethyl group, and wherein Y is dependent on Z and when Z is a carboxylic ester (COOR$_2$), Y represents a carboxylic moiety (COOR$_1$) wherein R$_1$ is a lithium, sodium or potassium cation or a primary alkyl group containing from 1 to 4 carbon atoms and preferably a methyl or ethyl group, cyano (—CN) and

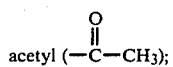

acetyl (—C—CH$_3$);

when Z is a cyano, phenyl or substituted phenyl group, Y represents cyano (—CN); and when Z is nitro (—NO$_2$), Y is hydrogen or methyl.

Additionally, the above objects are attained by the novel process of this invention to prepare the polyfunctional compounds of formula (I).

PROCESS FOR PREPARING THE NOVEL POLYFUNCTIONAL COMPOUNDS

This process is preferably substantially anhydrous and includes reacting by heating a salt of a monoalkyl ester of maleic acid with an active methylene or methine containing compound which is also referred to herein as the active hydrogen containing compound. The monoalkyl ester salt of maleic acid is of the general formula (II):

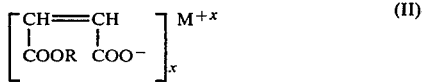

in which R and x are as previously defined and M represents calcium, magnesium, strontium, barium, sodium, potassium or lithium. In this process in the compound of formula (II) M cannot represent hydrogen whereas in formula (I) M$_1$ can represent hydrogen as well as the cations represented by M and thus the two separate designations of M and M$_1$ are utilized. The active hydrogen containing compound is of the general formula (III):

in which Y, O and Z are as previously defined.

The salts of the monoalkyl ester of maleic acid [formula (II)] employed in the process of this invention are prepared by treating a monoalkyl ester of maleic acid with a base. The monoalkyl ester of maleic acid is in turn readily available by reacting maleic anhydride with a lower alkyl alcohol having 1 to 4 carbon atoms, for example, methanol, ethanol, propanol and butanol. More specifically, maleic anhydride may be dissolved in the alcohol either at room temperature or by heating at an elevated temperature, e.g. about 50° C. to 60° C. Addition of the appropriate base, i.e. alkali metal or alkaline earth metal hydroxide such as sodium or potassium hydroxide or magnesium, barium, strontium or calcium hydroxide to a pH of about 7 to 9, neutralizes the acid portion of the molecule to produce the desired salt of formula (II). The monoalkyl maleate salt thus prepared is separated from the reaction mixture by conventional techniques, e.g. distillating off the alcohol under reduced pressure, or crystallization from the appropriate alcohol.

The active hydrogen containing compounds of formula (III) are known compounds. Malonate esters such as, for example, diethyl malonate and dimethyl malonate and cyanoacetate esters such as, for example, methyl cyanoacetate and ethyl cyanoacetate are preferred.

The subject invention, encompassing novel compounds and a novel process for their preparation, overcomes one or more of the disadvantages of the prior art heretofore described. This is accomplished with the advantage that such compounds may be easily prepared in good yield suitable for subsequent conversion into metal sequestering agents and, preferably, into either cis and trans aconitic acid or a mixture of isocitric acid, alloisocitric acid and the lactones of isocitric acid and alloisocitric acid.

The invention is hereinafter set forth in more details, specific features thereof being particularly delineated in the appended claims.

In the practice of the present invention a compound of formula (II) above is reacted preferably under substantially anhydrous conditions with a compound of formula (III) at an elevated temperature to form a reaction product which is the polyfunctional compound of formula (I) except for the cases wherein M$_1$=H. The latter compounds are obtained with an additional step involving acidification as will be more fully described hereinafter.

Since the ester group of the mono maleic ester salt (formula II) can hydrolyze in the presence of moisture to produce a non-reactive species (i.e. a mono salt of maleic acid), the reaction is preferably run under substantially anhydrous conditions. This can be accomplished by pre-drying the reactants and any reaction solvent by conventional means before carrying out the reaction.

Generally, the reaction of the compounds of formulae (II) and (III) to produce the novel compounds of formula (I) proceeds at temperatures of about 25° C. to 200° C. and more preferably between about 100° C. and 160° C. The actual reaction temperature will depend on whether a solvent is employed and the mutual solubilities of the reactants. Thus, if dimethyl formamide is utilized as the reaction solvent or cosolvent, a temperature as low as room temperature (about 25° C.) to about 100° C. can be utilized whereas if the active hydrogen containing compound of formula (III) is utilized in excess as both solvent and reactant, higher temperatures up to about 200° C. may be employed. Generally while reflux temperatures are normally operable, it is desirable to keep the temperature in the range of about 100° C. to 160° C. to maintain reasonable reaction rates and to avoid the reverse Michael reaction and other decomposition reactions which tend to take place at the higher temperatures.

The time necessary to complete the reaction is not critical. It will depend on temperatures, on the nature of the reactants, the solvent used, if any, concentration of the reactants and the homogencity of the system. Generally about one to three hours is sufficient to obtain the maximum yield.

The reaction takes place preferably in the liquid phase. Generally, the active hydrogen containing compound of formula (III) is a liquid and will dissolve the ester salt compound of formula (II). Since an excess of the reactant of formula (III) is beneficial to the reaction, such an excess is preferred as side reactions are minimized and eventual separation of the components is easier. Suitable active hydrogen compounds of formula (III), e.g. dimethyl malonate, methyl sodium malonate, diethyl malonate, dipropyl malonate, dibutyl malonate, phenyl acetonitrile, methyl cyanoacetate, ethyl cyanoacetate, nitroethane and the like may be utilized. Additionally, a co-solvent for both reactants may be used instead of an excess of the formula (III) compound provided the co-slvent does not contain an active hydrogen which will compete with the formula (III) compound under the reaction conditions and provided the co-solvent dissolves the reactants sufficiently to facilitate the reaction. Suitable solvents are, for example, dimethylformamide, dimethylacetamide and dimethyl sulfoxide.

The desired reaction product (i.e. compound of formula I) can be readily recovered from the reaction mixture by conventional methods such as for example by adding an insolubilizing liquid, e.g. ethyl ether. Upon the addition of a sufficient amount of such an insolubilizing liquid, the product precipitates out of solution and is readily separated from the reaction media by conventional means. The recovered product is sufficiently pure for conversion into the corresponding metal sequestrant salt. Upon filtration or vacuum distillation, washing, recrystallization if desired and drying, the desired product may be obtained in purer form. Alternatively, the acid form of the reaction product may be isolated by treating the reaction product with an aqueous solution of a mineral acid to liberate the carboxylic acid ($M_1=H$ in formula I) which is readily separated from the aqueous layer by extraction with a suitable solvent such as ethyl ether or by filtration in those cases where the carboxylic acid is a solid.

The present invention thus permits the synthesis of the desired polyfunctional compound of formula (I); further, in certain cases such compounds are produced in good yields. An additional advantage of this invention is that the novel products are obtained in readily recoverable form and that the novel synthesis or process permits the formation of the product without the use of added catalyst.

HYDROLYSIS OF SELECTED POLYFUNCTIONAL COMPOUNDS TO PRODUCE METAL ION SEQUESTRANTS AND DETERGENT BUILDERS

The compounds of formula (I), with the exception of those cases wherein Z is a nitro group, may be hydrolyzed under basic conditions to obtain the salt forms of the compounds represented by formula (IV) below. The acid forms of the compounds of formula (IV) are obtained by conventional acidification of the salt forms produced by the basic hydrolysis. Formula (IV) is as follows:

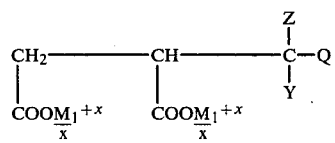

wherein Z, Q and Y are as previously defined and wherein $M_1$ represents hydrogen, sodium, potassium, lithium, calcium, magnesium, barium or strontium and x is 1 when $M_1$ is hydrogen or alkali metal and 2 when $M_1$ is alkaline earth metal. In those cases wherein Y and Z are carboxylic functions, i.e. $-COOR_1$ and $-COOR_2$ or a cyano group, alkaline hydrolysis converts each of the groups to a $-COOM_1^{+x}$ function wherein $M_1$ is an alkali metal or alkaline earth metal cation and x is as previously defined.

The alkaline hydrolysis is accomplished by heating the compounds of formula (I) with a stoichiometric amount or a slight excess of an alkali metal hydroxide, an alkaline earth metal hydroxide or an alkali metal carbonate in aqueous or aqueous alcoholic media. The hydrolysis is carried out at a pH of about 9–12, preferably about 10–11 and at a temperature of about 25° C. to about 100° C., preferbly about 40° C. to about 60° C. The preferred temperature and pH ranges in the hydrolysis procedure are used to maintain reasonable reaction rates and to minimize reverse Michael reactions.

Isolation of the salt forms of formula (IV) obtained by the above alkaline hydrolysis is carried out by conventional techniques such as solvent precipitation, evaporation, drying and recrystallization from suitable solvents such as alcohol-water.

In the cases where the alkaline earth metal salts of formula (IV) are produced, these may be converted into the alkali metal salt form by treatment with an aqueous solution of an alkali metal carbonate which precipitates the alkaline earth metal cations as the insoluble carbonate. The latter is then removed by filtration and the alkali metal salt of formula (IV) is isolated from the filtrate by conventional methods as previously described above.

Both the alkali metal and alkaline earth metal salt forms of formula (IV) may also be conventionally treated with a cation exchange resin to produce the acid forms of formula (IV) which may then be isolated by conventional methods such as extraction with a suitable solvent followed by evaporation of the solvent from the extract.

The acid forms of formula (IV) may be utilized as such (e.g. as metal ion sequestrants) or converted in the desired salt forms or mixture of acid and salt forms by neutralization with the required amount of the desired alkali metal hydroxide, ammonium hydroxide, an organic amine such as mono-, di- and tri-ethanolamine, morpholine and mixtures thereof. As previously indicated the alkali metal, ammonium and substitued ammonium salt forms of formula (IV) have utility as metal ion sequestrants and detergent builders.

CONVERSION OF SELECTED HYDROLYZED POLYFUNCTIONAL COMPOUNDS INTO TRICARBALLYLIC AND SUBSTITUTED TRICARBALLYLIC ACIDS AND THEIR SALTS

In the cases where the compounds of formula (IV) have the structure

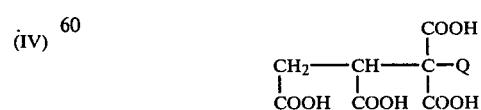

wherein Q is as previously defined, these compounds may be decarboxylated by heating alone at atmospheric pressure or under vacuum at temperatures greater than about 75° C., preferably about 75° C. to 175° C., depending on the decomposition point of the particular compound. Alternatively, decarboxylation of these compounds may be accomplished by heating the compounds with a dilute mineral acid solution, e.g. hydrochloric acid, at a pH of less than about 2 and under atmospheric pressure. These decarboxylation procedures produce tricarballylic acid and substituted tricarballylic acids having the formula

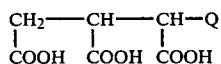

These acids may be neutralized with bases such as alkali metal hydroxides, ammonium hydroxide and alkylolamines to produce metal ion sequestrants and detergent builders.

ESTERIFICATION OF THE POLYFUNCTIONAL COMPOUNDS TO PRODUCE MIXED POLYESTER COMPOUNDS

In the case of the compounds of formula (I) wherein $M_1$ is H, these compounds may be completely esterified to produce mixed polyester compounds. This is accomplished by conventional reactions such as
1. reaction with diazomethane or
2. reaction with thionyl chloride followed by reaction with a normal alkanol of 1 to 12 carbons. The products produced have the formula:

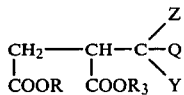

wherein $R_3$ is a normal alkyl group of 1 to 12 carbon atoms and wherein R, Z, Q and Y are as previously defined except that in the case where a cyano group is initially present it also becomes converted in the process scheme of 2 above to $COOR_3$. Similarly in those cases where Y is $COOR_1$ and $R_1$ is H, sodium, potassium or lithium, Y is converted to $COOR_3$.

HALOGENATION OF SELECTED POLYFUNCTIONAL COMPOUNDS

The compounds of formula (I) having the structure

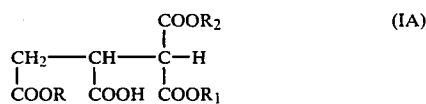

wherein R, $R_1$ and $R_2$ are as previously defined, can be halogenated with hypochlorous acid, hypobromous acid, sodium hypochlorite, sodium hypobromite, chlorine or bromine in aqueous or mixed aqueous/methanolic solution at pH's from about 2 to 8 to produce novel compounds having the following formula:

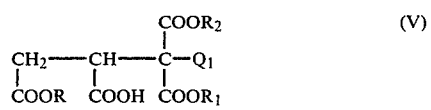

or salts thereof and wherein R, $R_1$ and $R_2$ are as previously defined and are preferably methyl or ethyl and $Q_1$ is Br or Cl and preferably chlorine.

The halogenation process is preferably carried out in an aqueous reaction medium. The compound of formula (IA) is introduced into a reaction vessel with water and, while stirring the mixture, a solution of a compound capable of generating HOX (wherein X=Cl or Br) is slowly added. The amount of reaction medium (i.e. water) used is not critical and is generally from about 50 to about 95% by weight of the total initial reaction mixture (i.e. compound IA plus water). The HOX required is conveniently generated from an alkali metal or alkaline earth metal hypohalite by acidification with a mineral acid solution such as hydrochloric or hydrobromic acid. Sodium hypochlorite or sodium hypobromite solutions are readily available as 5–15% solutions and are readily employed in this process. When the latter are used, the pH of the halogenation reaction mixture is controlled below about pH 8 and preferably between about 5 and about 7 by the simultaneous addition of a mineral acid. If bromine or chlorine is used in the halogenation reaction either directly or as bromine or chlorine water, the pH of the halogenation reaction mixture is maintained in the above range by the addition of alkali metal carbonates or hydroxides. The preferred pH range is utilized to maintain reasonable reaction rates.

The amount of HOX required in the halogenation process is about 1 to about 1.1 moles per mole of the compound of formula (IA). If a substantially greater ratio of HOX than 1.1 moles per mole of the compound of formula (IA) is utilized, it will not effect formation of the product but is uneconomical. If substantially less than one mole is employed, the reaction will not proceed to completion.

The temperature of the halogenation process is usually in the range from about 0° to 50° C. to avoid premature decarboxylation prior to halogenation of the compound and to avoid excessive loss of halogen which is in equilibrium with the hypohalous acid. Ambient temperatures are preferred as a matter of practicality and to keep side reactions to a minimum. After addition of the HOX reactant is complete, the reaction is monitored by periodic sampling and analysis by NMR. The characteristic NMR frequency of the methylene protons will shift from high field in the case of the compound of formula (IA) to a lower field as the halogenated compound of formula (V) is formed in the reaction mixture. When the desired degree of halogenation is obtained, the compound of formula (V) which is water soluble is isolated in its acid form by conventional methods involving acidification of the reaction mixture and extraction of the compound with a suitable organic solvent such as ethyl ether.

CONVERSION OF SELECTED HALOGENATED POLYFUNCTIONAL COMPOUNDS INTO A MIXTURE OF CIS AND TRANS ACONITIC ACID

The compounds of formula (V) may be "dehydrohalogenated" without isolation either under strongly alkaline conditions to produce a propene-1,1,2,3-tetracarboxylate which upon acidification decarboxylates to form aconitic acid (i.e. cis and trans aconitic acids) or under acidic aqueous conditions to produce directly a mixture of isocitric acid and alloisocitric acids and the lactones thereof. In both cases the "dehydrohalogenation" appears to proceed through an initial substitution of OH for the halogen followed by elimination of water under the alkaline conditions or decarboxylation under the acidic conditions.

In the case of "dehydrohalogenation" of the compound of formula (V), an aqueous solution of the formula (V) compound is neutralized and made alkaline to a pH of about 10 to about 12.6, preferably from about 11 to about 12, by the slow addition of an alkaline earth metal hydroxide selected from the group $Ca(OH)_2$, $Sr(OH)_2$ and $Pa(OH)_2$, preferably $Ca(OH)_2$. The alkaline solution is heated at about 25° C. to about 100° C. preferably about 50° C. to about 70° C. until "dehydrohalogenation" is complete, i.e. about ½ hour to 2 hours. The "dehydrohalogenation" is preferably monitored by NMR. This is done by sampling the solution, treating with excess $Na_2CO_3$, filtering the insoluble calcium carbonate that forms, evaporating the filtrate and examining the residue by NMR. The reaction is stopped at maximum formation of the propene 1,1,2,3 tetracarboxylate salt (VI) by observing the intensity of the chemical shift for the methylene protons on carbon 3 at about 3.34δ. The tetracarboxylate calcium salt in the reaction mixture is then treated with dilute mineral acid to liberate the free acid which then undergoes decarboxylation to produce a mixture of cis and trans aconitic acids. The reaction scheme for the above described preparation of cis/trans aconitic acids is thus as follows:

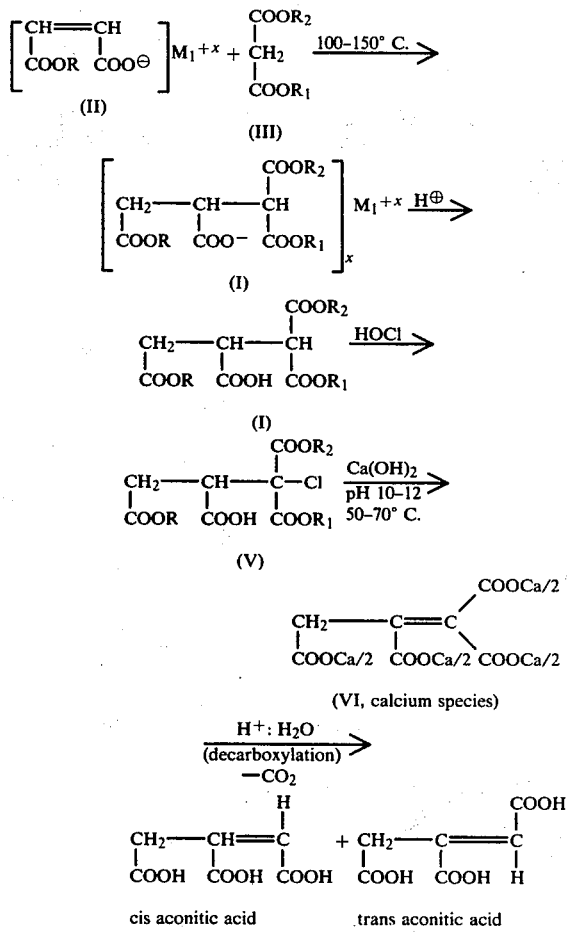

CONVERSION OF SELECTED HALOGENATION POLYFUNCTIONAL COMPOUNDS INTO A MIXTURE OF CIS AND TRANS ACONITIC ACID, ISOCITRIC ACID, ALLOISOCITRIC ACID AND THE LACTONES OF ISOCITRIC ACID AND ALLOISOCITRIC ACID

In the case where $Sr(OH)_2$ is used to "dehydrohalogenate" the compounds of structure V described above, it is possible to obtain a mixture of strontium salts of propene-1,1,2,3-tetracarboxylic acid and the 1-hydroxypropane-1,1,2,3-tetracarboxylic acid intermediate by following the reaction by NMR and stopping the reaction at the maximum formation of the propene-1,1,2,3-tetracarboxylate species (i.e. maximum intensity of the chemical shift for the methylene protons on carbon 3). On acidification with an aqueous solution of a mineral acid, e.g. hydrochloric acid, or treatment with a cation exchange resin in its acid cycle, decarboxylation occurs to give a mixture of cis and trans aconitic acid, isocitric acid, alloisocitric acid and the lactones of isocitric acid and alloisocitric acid. The mixture of products may be isolated by conventional techniques such as solvent extraction or by evaporation of the water followed by extraction with a suitable solvent such as acetone and subsequent evaporation of the acetone extract.

In the case where $Ba(OH)_2$ is used to "dehydrohalogenate" the compounds of structure V described above in the pH range 11-12, the reaction forms predominantly the 1-hydroxypropane-1,1,2,3-tetracarboxylate species as the barium salt. On acidification with an aqueous solution of a mineral acid, e.g. hydrochloric acid, or treatment with a cation exchange resin in the acid cycle, decarboxylation occurs to give a mixture of isocitric acid, alloisocitric acid and the lactones of isocitric acid and alloisocitric acid together with some cis and trans aconitic acid.

CONVERSION OF SELECTED HALOGENATED POLYFUNCTIONAL COMPOUNDS INTO A MIXTURE OF ISOCITRIC ACID, ALLOISOCITRIC ACID AND THE LACTONES THEREOF

In the special case where the compounds of structure V are reacted with $Mg(OH)_2$ in aqueous medium, a pH of only about 8-9 is achievable. Under these conditions and between temperatures of about 25° C. and about 105° C., preferably from 90°-105° C., the halogen atom is substituted by a hydroxyl group with simultaneous decarboxylation as well as saponification (with sufficient $Mg(OH)_2$) to give a mixture of the magnesium salts of isocitric acid and alloisocitric acid. The latter salts may then be converted into the acid and lactone forms by either treatment with a suitble cation exchange resin or acidification with mineral acid and isolation by conventional techniques such as solvent extraction or evaporation of the water present followed by extraction of the residue with a solvent such as acetone and subsequent evaporation of the acetone extract.

Alternatively, the compounds of structure V may be treated under weakly alkaline conditions of about pH 8-9 utilizing an aqueous solution containing the stoichiometric amount (one equivalent per mole of V) of alkali metal hydroxide or alkaline earth metal hydroxide at temperatures between 25° C. and 75° C. Under these conditions a novel β-lactone ester of the following structure is obtained:

$$\underset{\text{(VII)}}{\begin{array}{c}\phantom{CH_2\!-\!\!-\!\!-\!CH\!-\!}\diagup COOR_2\\ CH_2\!-\!\!-\!CH\!-\!C\\ \phantom{CH_2\!-\!\!-\!\!-\!CH\!-\!}|\phantom{\diagup}\diagdown\\ COOR\phantom{-}\underset{\overset{\|}{O}}{C}\!-\!\!-\!O\phantom{-}COOR_1\end{array}}$$

wherein R, $R_1$ and $R_2$ are as previously defined. In place of the alkali metal or alkaline earth metal hydroxides, a weak organic base such as pyridine or triethylamine may also be reacted with compounds of structure V under anhydrous conditions to produce the same product (i.e. compound VII).

In another embodiment, an aqueous solution of an alkali metal carbonate with or without an auxiliary organic base such as pyridine is reacted with a compound of formula V to produce a compound of formula VIII:

$$\underset{\text{(VIII)}}{\begin{array}{c}\phantom{CH_2\!-\!\!-\!CH\!-\!}\diagup COOR_2\\ CH_2\!-\!\!-\!CH\!-\!C\\ \phantom{CH_2\!-\!\!-\!CH\!-\!}|\phantom{\diagup}\diagdown\\ COOR\phantom{-}COOM\phantom{-}OH\phantom{-}COOR_1\end{array}}$$

wherein R, $R_1$ and $R_2$ as previously defined and M is an alkali metal cation selected from the group lithium, sodium and potassium.

The compound of structures (VII) and (VIII) may be readily hydrolyzed by heating with the appropriate amount of aqueous solution of an alkali metal hydroxide, alkali metal carbonate or an alkaline earth metal hydroxide at a pH of about 9–11 and preferably between about 9 and 10 to produce tetracarboxylate salts having the following structure:

$$\underset{\text{(IX)}}{\begin{array}{c}\phantom{CH_2\!-\!\!-\!\!-\!CH\!-\!\!-\!\!-\!}COOM_2^{+x}/x\\ \phantom{CH_2\!-\!\!-\!\!-\!CH\!-\!\!-\!\!-\!}|\\ CH_2\!-\!\!-\!\!-\!\!-\!CH\!-\!\!-\!\!-\!\!-\!C\!-\!OH\\ |\phantom{\!-\!\!-\!\!-\!\!-\!}|\phantom{\!-\!\!-\!\!-\!\!-\!}|\\ COOM_2^{+x}/x\phantom{-}COOM_2^{+x}/x\phantom{-}COOM_2^{+x}/x\end{array}}$$

wherein $M_2$ is Li, Na or K or an alkaline earth metal cation selected from the group Ca, Sr and Ba and x is 1 or 2 and corresponds to the valence of the cation $M_2$.

The compounds of formula (IX) wherein $M_2$ is Ca, Sr or Ba may also be treated with a solution of an alkali metal carbonate to produce the corresponding alkali metal salts (i.e. formula (IX) wherein $M_2$ is Li, Na or K and x=1). The alkali metal salts of formula (IX) are useful as detergent builders and metal ion sequestrants.

The compounds of formula (IX) may each be converted into a mixture of isocitric acid, alloisocitric acid and the lactones of isocitric acid and alloisocitric acid by acidification with a dilute solution of a mineral acid such as hydrochloric acid, whereby decarboxylation occurs to produce the said mixture of products.

In another preferred embodiment the halogenated species of formula (V) may be heated with an aqueous solution of mineral acid, e.g. refluxing with 10% hydrochloric acid for about 1 to about 16 hours to simultaneously hydrolyze the ester groups, dehydrohalogenate and decarboxylate the compound to produce a mixture of isocitric acid, alloisocitric acid and the lactones thereof. The temperature of reaction is about 25° C. to about 110° C., preferably about 90° C. to 100° C. The reaction is run for a sufficient amount of time to result in the desired end product, usually about 6 hours to about 10 hours.

The reaction scheme thus is the same as that for aconitic acid up to the product of formula (V). The remaining sequences is as follows:

$$\begin{array}{c}\phantom{CH_2\!-\!\!-\!\!-\!CH\!-\!\!-\!}COOR_2\\ \phantom{CH_2\!-\!\!-\!\!-\!CH\!-\!\!-\!}|\\ CH_2\!-\!\!-\!\!-\!CH\!-\!\!-\!C\!-\!Cl\\ |\phantom{-\!\!-\!\!-\!}|\phantom{-\!\!-\!\!-\!}|\\ COOR\phantom{-}COOH\phantom{-}COOR_1\end{array}\xrightarrow[-HCl]{\underset{-CO_2;}{H^+/H_2O}}$$

$$\begin{array}{c}\phantom{CH_2\!-\!\!-\!}OH\\ \phantom{CH_2\!-\!\!-\!}|\\ CH_2\!-\!\!-\!CH\!-\!\!-\!CH\\ |\phantom{\!-\!\!-\!}|\phantom{\!-\!\!-\!}|\\ COOH\phantom{-}COOH\phantom{-}COOH\end{array}+\begin{array}{c}\phantom{CH_2\!-\!\!-\!}COOH\\ \phantom{CH_2\!-\!\!-\!}|\\ CH_2\!-\!\!-\!CH\!-\!\!-\!CH\\ |\phantom{\!-\!\!-\!}|\phantom{\!-\!\!-\!}|\\ COOH\phantom{-}COOH\phantom{-}OH\end{array}\begin{array}{c}\text{lactones}\\ +\text{ of both}\\ \text{acids}\end{array}$$

isocitric acid  alloisocitric acid

Representative compounds of formula (I) prepared according to the process of the invention include 1-Calcium Bis[Methyl α-(dimethyl malonyl)succinate]

$$\left[\begin{array}{c}CH_2\!-\!\!-\!\!-\!\!-\!CH\!-\!CH(COOCH_3)_2\\ |\phantom{\!-\!\!-\!\!-\!\!-\!\!-\!}|\\ COOCH_3\phantom{-}COOH\end{array}\right]_2 Ca$$

2-Ethyl sodium α-(diethyl malonyl)succinate $$\begin{array}{c}CH_2\!-\!\!-\!\!-\!\!-\!\!-\!CH\!-\!CH(COOCH_2CH_3)_2\\ |\phantom{\!-\!\!-\!\!-\!\!-\!\!-\!}|\\ COOCH_2CH_3\phantom{-}COONa\end{array}$$

3-Methyl hydrogen α-(diethyl malonyl)succinate $$\begin{array}{c}CH_2\!-\!\!-\!\!-\!\!-\!\!-\!CH\!-\!CH(COOCH_2CH_3)_2\\ |\phantom{\!-\!\!-\!\!-\!\!-\!\!-\!}|\\ COOCH_3\phantom{-}COOH\end{array}$$

4-Ethyl hydrogen α-(dimethyl malonyl)succinate $$\begin{array}{c}CH_2\!-\!\!-\!\!-\!\!-\!\!-\!CH\!-\!CH(COOCH_3)_2\\ |\phantom{\!-\!\!-\!\!-\!\!-\!\!-\!}|\\ COOCH_2CH_3\phantom{-}COOH\end{array}$$

5-Methyl hydrogen α-(1-nitroethyl)succinate $$\begin{array}{c}\phantom{CH_2\!-\!\!-\!\!-\!\!-\!CH\!-\!}\diagup CH_3\\ CH_2\!-\!\!-\!\!-\!\!-\!CH\!-\!CH\\ |\phantom{\!-\!\!-\!\!-\!}|\phantom{-}\diagdown\\ COOCH_3\phantom{-}COOH\phantom{-}NO_2\end{array}$$

6-Methyl hydrogen α-(acetyl carboethyl methinyl)-succinate $$\begin{array}{c}\phantom{CH_2\!-\!\!-\!\!-\!CH\!-\!\!-\!CH\!-\!}O\\ \phantom{CH_2\!-\!\!-\!\!-\!CH\!-\!\!-\!CH\!-\!}\|\\ CH_2\!-\!\!-\!\!-\!CH\!-\!\!-\!CH\!-\!C\!-\!CH_3\\ |\phantom{\!-\!\!-\!\!-\!}|\phantom{\!-\!\!-\!}|\\ COOCH_3\phantom{-}COOH\phantom{-}COOCH_2CH_3\end{array}$$

7-Methyl hydrogen α-(cyanobenzyl)succinate $$\begin{array}{c}CH_2\!-\!\!-\!\!-\!\!-\!CH\!-\!\!-\!CH\!-\!\!-\!\text{C}_6\text{H}_5\\ |\phantom{\!-\!\!-\!\!-\!\!-\!}|\phantom{\!-\!\!-\!}|\\ COOCH_3\phantom{-}COOH\phantom{-}CN\end{array}$$

8-Methyl hydrogen α-(cyano carboethoxy methinyl)-succinate $$\begin{array}{c}\phantom{CH_2\!-\!\!-\!\!-\!CH\!-\!}\diagup CN\\ CH_2\!-\!\!-\!\!-\!CH\!-\!CH\\ |\phantom{\!-\!\!-\!\!-\!}|\phantom{-}\diagdown\\ COOCH_3\phantom{-}COOH\phantom{-}COOCH_2CH_3\end{array}$$

9-Methyl sodium α-(methyl sodium malonyl)succinate $$\begin{array}{c}CH_2\!-\!\!-\!\!-\!\!-\!CH\!-\!\!-\!CH\!-\!\!-\!COOCH_3\\ |\phantom{\!-\!\!-\!\!-\!\!-\!}|\phantom{\!-\!\!-\!}|\\ COOCH_3\phantom{-}COONa\phantom{-}COONa\end{array}$$

10-Potassium butane-1,2,2,4-tetracarboxylic methyl ester-3-carboxylate

-continued $$\text{CH}_2\text{---CH---C---CH} \\ |\quad\quad |\quad\quad |\quad\quad | \\ \text{COOCH}_3\ \text{COOK}\ \text{COOCH}_3\ \text{COOCH}_3$$
(with COOCH₃ on top of the C)

Representative compounds of formula V are as follows:

1-Methyl hydrogen α-(dimethyl chloromalonyl)succinate $$\text{CH}_2\text{---CH---C---(COOCH}_3)_2 \\ |\quad\quad |\quad\quad | \\ \text{COOCH}_3\ \text{COOH}\ \text{Cl}$$

2-Ethyl hydrogen α-(diethyl chloromalonyl)succinate $$\text{CH}_2\text{---CH---C---(COOCH}_2\text{CH}_3)_2 \\ |\quad\quad |\quad\quad | \\ \text{COOCH}_2\text{CH}_3\ \text{COOH}\ \text{Cl}$$

3-Methyl hydrogen α-(diethyl-2-chloromalonyl)succinate $$\text{CH}_2\text{---CH---C---(COOCH}_2\text{CH}_3)_2 \\ |\quad\quad |\quad\quad | \\ \text{COOCH}_3\ \text{COOH}\ \text{Cl}$$

4-Ethyl hydrogen α-(dimethyl chloromalonyl)succinate $$\text{CH}_2\text{---CH---C---Cl} \\ |\quad\quad |\quad\quad | \\ \text{COOCH}_2\text{CH}_3\ \text{COOH}\ \text{COOCH}_3$$
(with COOCH₃ on top of the C)

5-Methyl hydrogen α-(dimethyl bromomalonyl)succinate $$\text{CH}_2\text{---CH---C---(COOCH}_3)_2 \\ |\quad\quad |\quad\quad | \\ \text{COOCH}_3\ \text{COOH}\ \text{Br}$$

Representative compounds of formulas (VI), (VII), (VIII) and (IX) obtained from the halogenated compounds of formula (V) are as follows:

1-Tetrasodium propene-1,1,2,3-tetracarboxylate $$\text{CH}_2\text{---C===C---COONa} \\ |\quad\quad |\quad\quad | \\ \text{COONa}\ \text{COONa}\ \text{COONa}$$
(example of formula VI)

2-Methyl hydrogen α-(dimethyl hydroxymalonyl)-succinate β-lactone $$\text{CH}_2\text{---CH} \diagdown\text{COOCH}_3 \\ |\quad\quad\quad\quad\quad\diagup \\ \text{COOCH}_3\ \text{C---O}\ \text{COOCH}_3 \\ \quad\quad\quad \|\ \\ \quad\quad\quad \text{O}$$
(example of formula VII)

3-Ethyl hydrogen α-(diethyl hydroxymalonyl)succinate β-lactone $$\text{CH}_2\text{---CH} \diagdown\text{COOCH}_2\text{CH}_3 \\ |\quad\quad\quad\quad\quad\diagup \\ \text{COOCH}_2\text{CH}_3\ \text{C---O}\ \text{COOCH}_2\text{CH}_3 \\ \quad\quad\quad \|\ \\ \quad\quad\quad \text{O}$$
(example of formula VII)

4-Ethyl hydrogen α-(diethyl hydroxymalonyl) succinate $$\text{CH}_2\text{---CH} \diagdown\text{COOCH}_2\text{CH}_3 \\ |\quad\quad |\quad\quad\quad \\ \text{COOCH}_2\text{CH}_3\ \text{COONa}\ \text{OH} \\ \quad\quad\quad\quad\quad \text{COOCH}_2\text{CH}_3$$
(example of formula VIII)

5-Dicalcium 1-hydroxy propane-1,1,2,3-tetracarboxylate $$\text{CH}_2\text{---CH---C} \diagdown\text{COOCa/2} \\ |\quad\quad |\quad\quad\quad \\ \text{COOCa/2}\ \text{COOCa/2}\ \text{OH} \\ \quad\quad\quad\quad\quad \text{COOCa/2}$$
(example of formula IX)

6-Tetrasodium propane-1-hydroxy-1,1,2,3-tetracarboxylate $$\text{CH}_2\text{---CH} \diagdown\text{COONa} \\ |\quad\quad |\quad\quad\quad \\ \text{COONa}\ \text{COONa}\ \text{OH} \\ \quad\quad\quad\quad\quad \text{COONa}$$
(example of formula IX)

The following examples will more fully illustrate the embodiments of this invention. All parts and proportions referred to herein and in the appended claims are by weight unless otherwise indicated.

EXAMPLE I

A. Preparation of Sodium Methyl Maleate

One mole of maleic anhydride is dissolved in 1000 ml methanol and 0.5 mole of sodium carbonate is added. The solution is filtered and the methanol is distilled off under pressure. After drying the product in a vacuum oven, 152 g of sodium methyl maleate is obtained.

B. Preparation of Calcium Bis(Methyl Maleate)

$$\left[\begin{array}{c}\text{CH}===\text{CH} \\ |\quad\quad\quad | \\ \text{COOCH}_3\ \text{COO}^-\end{array}\right]_2 \text{Ca}^{++}$$

One mole of maleic anhydride is dissolved with stirring in 1000 ml methanol at 50°–60° C. The mixture is cooled to 25° C. and with the aid of a pH meter, the pH is adjusted to 8.6 with calcium hydroxide while maintaining the temperature below 25° C. with an ice bath. 149 g of calcium bis(methyl maleate) is recovered by crystallizing out of methanol followed by drying in a vacuum oven.

C. Preparation of Lithium Methyl Maleate

Twenty grams of maleic anhydride is dissolved in 200 mls methanol, 4.8 grams (0.2 moles) lithium hydroxide is added. The mixture is stirred until all the lithium hydroxide dissolves (at this point the pH reads 7.0). To the solution is added acetone and the solid is filtered and dried. 23 grams product is obtained.

D. Preparation of Potassium Methyl Maleate 46.5 grams (0.46 mole) maleic anhydride is dissolved in 500 mls methanol. 36 g $K_2CO_3$ is added to a pH of 8.5–8.6, the solution is filtered and evaporated to dryness. 77.6 grams of product is obtained. Purity=96.4% by NMR analysis.

E. Preparation of Sodium Ethyl Maleate

Fifty-seven grams (0.57 moles) maleic anhydride is dissolved in 500 mls ethanol. With the aid of a pH meter the pH is adjusted to 8.5–8.6 with sodium carbonate. The solution is evaporated on the roto evaporator and dried in a vacuum oven. Ninety-four grams (0.57 moles) of product having a purity of 99.4% (NMR analysis) is obtained.

EXAMPLE II

Preparation of Methyl Hydrogen α-(Dimethyl Malonyl)Succinate

Method A

Into a 500 ml, one neck flask equipped with magnetic stirrer is placed 100 grams sodium methyl maleate and 350 grams dimethyl malonate. The reaction temperature is maintained at 100°–105° C. for 5 hours. The excess malonate is distilled off under vacuum and the residue is extracted with ether:acetone (5:1) to remove unreacted malonate and thereby leaving a gummy residue of the sodium salt of the title compound. The latter is then dissolved in water, acidified with 1:1 sulfuric acid and the resulting liquid organic layer is separated from the water layer. On standing this liquid crystallizes. The total solid, 180 grams, is extracted with hexane to remove any malonate and the solid is dried. Yield: 153 grams. The water soluble fraction from above is evaporated to dryness and extracted with hexane. Ten grams of additional product is obtained in this manner. Total yield: 163 grams (94% of theoretical).

Method B

Fifty grams sodium methyl maleate is mixed with 200 grams dimethyl malonate in a 500 ml one neck flask equipped with a magnetic stirrer. The temperature is maintained at 100°–105° C. for 4 hours, then the excess malonate is distilled off under vacuum. The viscous liquid obtained is dissolved in water and 0.33 moles sulfuric acid in 25 mls water is added. The liquid separates and crystallizes on standing. The entire solution including the crystals is filtered and the product is washed with water leaving a white solid (23 grams). The water layer is extracted with ether and the ether distilled off. On standing the residue crystallizes; yield: 12.5 grams, m.p. 101.5° C. Total yield of product: 35.5 grams.

Method C 24.3 grams (0.145 mole) potassium methyl maleate is added to 100 g of dimethyl malonate. The mixture is heated to 110°–115° C. for 4–5 hours. Complete solution is attained in 3–4 hours. The reaction solution is then distilled under pressure to remove excess dimethyl malonate. The distillation residue is dissolved in 200 mls water and acidified with 15 g conc. HCl in 25 mls water. The resulting organic layer is extracted with ethyl ether and the ethereal extract evaporated to give a residue of 42 g (theoretical: 39 grams). The product crystallizes on standing.

The structure of the products obtained by the three methods is confirmed by NMR analysis (CDCl$_3$) to correspond to the title compound:

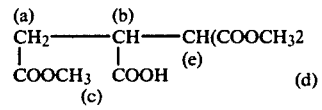

CH$_2$(a) ABX multiplet, two peaks, one at 2.76δ, one at 2.86δ
CH(b) multiplet, 3.44–3.70δ
CH$_3$(c) singlet at 3.70δ
CH$_3$(d) singlet at 3.76δ
CH(e) doublet centered at 3.99δ

EXAMPLE III

Preparation of Methyl Hydrogen α-(Diethyl Malonyl)Succinate

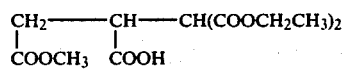

Ninety grams of sodium methyl maleate is reacted with 200 grams of diethyl malonate at 100°–110° C. for four hours. After the reaction mixture is cooled to 25° C., 1000 mls of water is added and the unreacted diethyl malonate layer is separated. The aqueous layer is acidified with a mixture of 61 g of conc. hydrochloric acid and 50 mls water and the organic layer is separated. The organic layer is dissolved in ether and washed with water to remove dissolved methyl hydrogen maleate. The ether is then distilled off, obtaining 95 grams (55% yield) of product. The structure is confirmed by NMR analysis (CDCl$_3$):

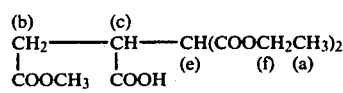

CH$_3$(a) triplet centered at 1.25δ
CH$_2$(b) doublet (ABX) one peak at 2.75δ, one at 2.83δ
CH(c) multiplet, 3.43–3.78δ
CH$_3$(d) singlet, 3.67δ
CH(e) doublet centered at 3.92δ
CH$_2$(f) quartet centered at 4.19δ

EXAMPLE IV

Preparation of Ethyl Hydrogen α-(Diethyl Malonyl)Succinate

One hundred grams of sodium ethyl maleate is reacted with 500 grams of diethyl malonate at 100°–110° C. for 5 hours. The solution is cooled and is mixed with 1000 mls water. The aqueous layer is separated and acidified with 110 grams of 6.5 N hydrochloric acid. The liquid organic layer which separates is dissolved in ether and extracted twice with water to remove ethyl hydrogen maleate. After evaporation of the ether, a residue of 140 g (46% yield) of the title compound is obtained. The structure is confirmed by NMR analysis (CDCl$_3$):

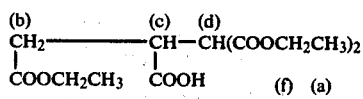

(e) (a)
CH₃(a) triplet, 1.1–1.45δ
CH₂(b) doublet centered at 2.67δ
CH(c) multiplet centered at 3.60δ
CH(d) doublet centered at 3.92δ
CH₂(e) quartet centered at 4.15δ
CH₂(f) quartet centered at 4.20δ

EXAMPLE V

Preparation of Ethyl Hydrogen α-(Dimethyl Malonyl)Succinate

Twenty five grams (0.15 mole) of sodium ethyl maleate (of 99.4% purity) is mixed with 100 grams of dimethyl malonate and the solution heated at 100°–107° C. for 6 hours. The solution is then evaporated under reduced pressure to remove excess dimethyl malonate. The distillation residue is dissolved in 200 mls water and acidified with 40 g of 4.5 N hydrochloric acid. The product which separates as a liquid, is extracted with 100 mls chloroform and the chloroform extract is distilled under reduced pressure. Forty five grams of a liquid product is obtained as a residue. NMR analysis (CDCl₃) is consistent with the title compound containing traces of dimethyl malonate:

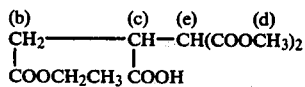

CH₃(a) triplet centered at 1.22δ
CH₂(b) ABX doublet, 2.55–2.87δ
CH(c) ABX multiplet, 3.15–3.57δ
CH₃(d) singlet, 3.75δ
CH(e) doublet centered at 3.93δ
CH₂(f) quartet centered at 4.12δ

EXAMPLE VI

Preparation of Methyl Hydrogen α-(Acetyl Carpoethoxy Methinyl)Succinate

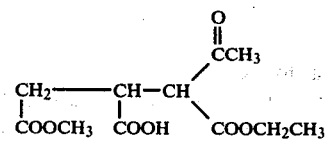

Into a 100 ml, one neck flask equipped with a magnetic stirrer is placed 10 grams sodium methyl maleate and 40 grams ethyl acetoacetate. The mixture is heated to 110° C. for 45 minutes. Water, 200 mls, is then added to the reaction mixture and the upper layer, consisting of ethyl acetoacetate, is removed. The water layer is acidified with a mixture of 7 grams conc. H₂SO₄ and 10 mls water. The liquid that separates is extracted with ether and the ether extract is distilled in vacuo to leave a viscous residue. The residue is extracted 4–5 times with hot hexane to remove ethyl acetoacetate and leaving behind 14 grams (77.8% of theoretical) of the title compound (neutralization equivalent found, 264). NMR analysis (CDCl₃) of the product confirms the structure and shows the product to consist of a 58:42 weight ratio of keto:enol forms:

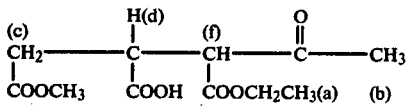

CH₃(a) triplet centered at 1.27δ
CH₃(b) singlet, 2.28δ
CH₂(c) ABX multiplet, 2.57–2.88δ broad
CH(d) multiplet, 3.46–3.81δ
COOCH₃(e) singlet, 3.60δ
CH(f) doublet, 3.90–4.09δ
COOCH₂(g) quartet centered at 4.16δ

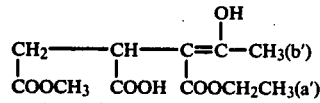

CH₃(a') triplet centered at 1.25δ
CH₃(b') singlet at 1.82δ

All other spectral assignments are the same as for the keto form.

EXAMPLE VII

A. Preparation of Lithium Methyl α-(Cyano Carboethoxy Methinyl)Succinate

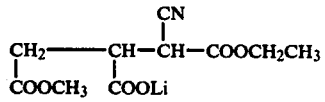

Fifty grams (0.38 mole) of lithium methyl maleate is dissolved in a mixture of 150 grams cyanoacetate and 100 grams DMF (dimethyl formamide) at 80°–90° C. The temperature is then raised to 100°–105° C. for 45 minutes. The solution is evaporated in vacuo to remove excess solvents and the residue is extracted twice with 500 mls ether to leave 96 grams of the title compound as a gummy residue. The structure is confirmed by NMR analysis (D₂O):

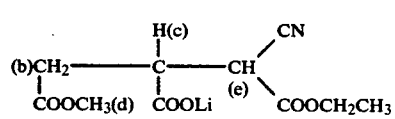

CH₃(a) triplet centered at 1.15δ
CH₂(b) multiplet, 2.69–3.05δ
CH(c) multiplet, 3.25–3.48δ
CH₃(d) singlet, 3.68δ
CH(e) hidden under CH₂(f) group
CH₂(f) quartet centered at 4.24δ

B. Preparation of Methyl Hydrogen α-(Cyanocarboethoxy Methinyl)Succinate

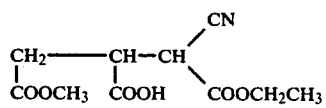

Ninety six grams of the product obtained above in VII(A) is dissolved in water and a mixture of 38 grams conc. hydrochloric acid in 50 mls water is added to the solution. The product which separates is extracted with ether. Evaporation of the ether extract yields 74 grams of product containing traces of ethyl cyanoacetate and DMF. NMR analysis (CDCl₃) confirms the structure:

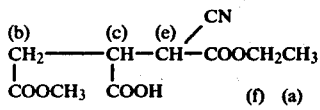

(d)
CH₃(a) triplet centered at 1.33δ
CH₂(b) multiplet at 2.98–3.08δ
CH(c) multiplet at 3.35–3.70δ
CH₃(d) singlet, 3.72δ
CH(e) doublet centered at 4.25δ
CH₂(f) quartet centered at 4.30δ

EXAMPLE VIII

Preparation of Methyl Hydrogen α-(Cyanobenzyl)Succinate

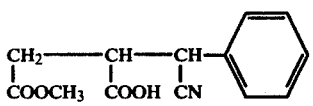

Into a 200 ml, one-neck flask is placed 35 grams of sodium methyl maleate (0.23 moles), 85 grams (0.73 moles) of phenyl acetonitrile and 80 g (1.1 moles) dimethyl formamide. The reaction mixture is heated to 135°–140° C. for five hours and then distilled in vacuo. The residue is extracted three time with 300 ml ether. The solid (56 grams) is then dissolved in water and acidified with 23 grams conc. HCl in 50 mls water. The liquid that separates out is dissolved in ether and washed with water to remove unreacted starting materials. The ether is distilled off to give a residue of 50 grams of product (yield: 88%). The structure is verified by NMR (in CDCl₃):

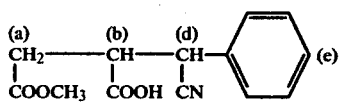

CH₂(a) ABX multiplet at 2.50–3.00δ
CH(b) multiplet, 3.30–3.56δ
CH₃(c) singlet, 3.67δ
CH(d) multiplet, 4.20–4.60δ
CH(e) (phenyl) at 7.35δ

EXAMPLE IX

Preparation of Methyl Hydrogen α-(1 Nitroethyl)Succinate

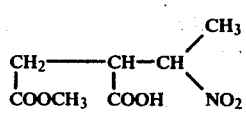

Into a 100 ml, one neck flask is placed 10 grams of sodium methyl maleate, 60 mls N,N-dimethyl formamide (DMF) and 40 grams nitroethane. The solution is heated at 60° C. for two hours and then partially distilled in vacuo to remove the DMF and nitroethane. The residue, by NMR analysis (D₂O), has the following structure:

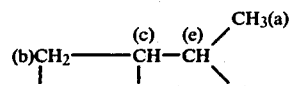

(d)
CH₃(a) doublet of doublets { one centered at 1.44δ
                              one centered at 1.57δ
CH₂(b) multiplet, 2.5–2.72δ
CH(c) multiplet centered at 3.25δ
CH₃(d) singlet, 3.65δ
CH(e) multiplet, 4.77–5.1δ

The residue from above is dissolved in water and acidified with 7 mls conc. hydrochloric acid. The water is distilled off and the residue is extracted with acetone. The acetone is evaporated and the liquid residue is extracted with hexane to remove dissolved DMF. The residue is then triturated with ether, filtered and the ether is removed under vacuum. Five grams (14% yield) of product is obtained. The structure is confirmed by NMR analysis (CDCl₃):

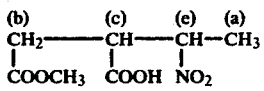

(d)
CH₃(a) doublet of doublets { one centered at 1.56δ
                              one centered at 1.78δ
CH₂(b) multiplet, 2.6–2.9δ
CH(c) multiplet, 3.32–3.64δ
CH₃(d) singlet, 3.65δ
CH(e) multiplet centered at 5.0δ

EXAMPLE X

Preparation of Sodium Methyl α-(Methyl Sodium Malonyl)Succinate

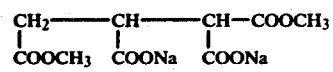

Sodium methyl malonate

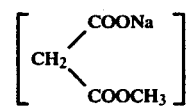

is prepared as follows:
One mole of dimethyl malonate is dissolved in 100 mls methanol and ½ mole of NaOH dissolved in 100 mls of methanol is added. The solution is stirred for 6 hours, the methanol is evaporated off and the solid filtered and washed with ether. One mole of sodium methyl malonate is recovered.

Twenty grams of the sodium methyl malonate (0.14 mole) and 15 grams (0.1 mole) sodium methyl maleate are mixed with 100 grams of dimethyl formamide (DMF) and the mixture heated at 115°–118° C. for ½ hour while stirring the mixture. The reaction mixture is then cooled and 100 mls of acetone is added to extract out DMF. The solid is triturated first with 400 mls of ether and then with 400 mls of 1:1 acetone:ether. Twenty six grams (73% yield) of product is obtained.

NMR analysis of the product in D₂O confirms the structure and in addition shows the presence of some fumarate and malonate:

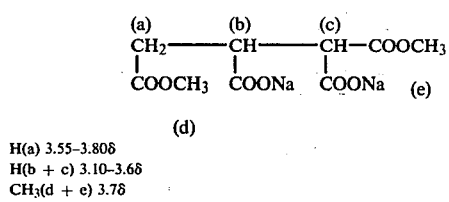

H(a) 3.55–3.80δ
H(b + c) 3.10–3.6δ
CH₃(d + e) 3.7δ

EXAMPLE XI

Preparation of Methyl Hydrogen Tetramethyl Butane-1,2,2,4-Tetracarboxylate-3-Carboxylic Acid

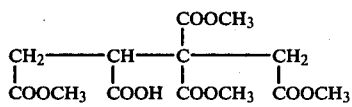

A mixture of 16.8 g (0.1 mole) of potassium methyl maleate and 50 g of trimethyl ethane-1,1,3-tricarboxylate is heated at 140° C. for 5 hours. The reaction mixture is cooled and mixed with 200 ml of water and 200 ml of ethyl ether. After shaking the mixture, the water layer, which contains the potassium salt of the title compound, is separated and acidified with 10 g of concentrated hydrochloric acid. The acidified mixture is extracted with ethyl ether and the ether layer is evaporated to give 16 g of the title compound. The structure of the compound is confirmed by NMR (CDCl₃):

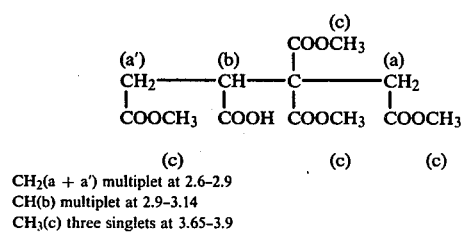

CH₂(a + a') multiplet at 2.6–2.9
CH(b) multiplet at 2.9–3.14
CH₃(c) three singlets at 3.65–3.9

EXAMPLE XII

Preparation of Methyl Hydrogen α-(Dimethyl Chloromalonyl)Succinate

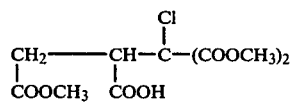

Thirteen grams (0.05 moles) of the product prepared in Example II, i.e. methyl hydrogen α-(dimethyl malonyl)succinate, is dissolved in 150 mls of water. Sodium hypochlorite, 70 grams of a 5.25% by weight solution, is added slowly while stirring the solution during a 15 minute period until the pH rises to 7.0. The solution is then acidified to pH 1.9 and is extracted with ether. The ether extract is evaporated to give fifteen grams of the title compound as a liquid. NMR analysis (CDCl₃) confirms the structure:

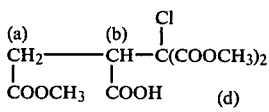

CH₂(a) multiplet consisting of a doublet and singlet 2.83–3.04δ
CH(b) doublet of doublets, 4.04–4.30δ
COOCH₃(c) singlet at 3.74δ
COOCH₃(d) singlet at 3.87δ

EXAMPLE XIII

Preparation of Methyl Hydrogen α-(Diethyl Chloromalonyl)-Succinate

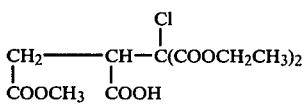

Into a beaker is placed 90 grams of the product prepared in Example III, i.e. methyl hydrogen α-(diethyl malonyl)succinate, and 200 mls water. 500 mls of NaOCl solution (5.25% by weight) is added slowly during a ½ hour period to a pH of 7.0. The solution is then acidified with dilute hydrochloric acid (10%), to a pH of 1.0 and extracted with ether. The ether extract is evaporated to give 95 g (95% yield) of the title compound as a syrupy residue. The structure is confirmed by NMR analysis (CDCl₃):

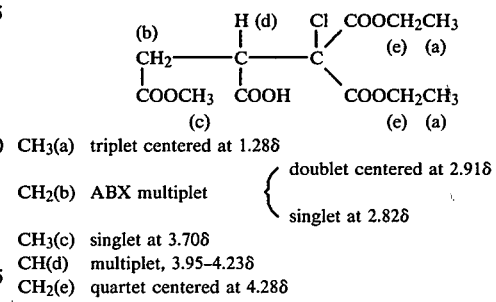

CH₃(a) triplet centered at 1.28δ

CH₂(b) ABX multiplet { doublet centered at 2.91δ
                      singlet at 2.82δ

CH₃(c) singlet at 3.70δ
CH(d) multiplet, 3.95–4.23δ
CH₂(e) quartet centered at 4.28δ

EXAMPLE XIV

Preparation of Ethyl Hydrogen α-(Diethyl Chloromalonyl)-Succinate

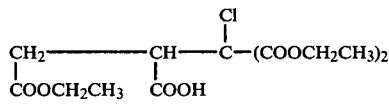

One hundred grams of the compound prepared in Example IV, i.e. ethyl hydrogen α-(diethyl malonyl)-succinate, is mixed with 300 mls water. Five hundred mls of (5.25% by weight) sodium hypochlorite is added during 45 minute period to a pH of 7.0. The solution is then acidified to a pH of 1 with dilute (10%) hydrochloric acid and the product which separates is extracted with ether. The ether extracts are evaporated to give 92 g (82% yield) of the title product as a syrupy residue. The structure is confirmed by NMR analysis (CDCl₃):

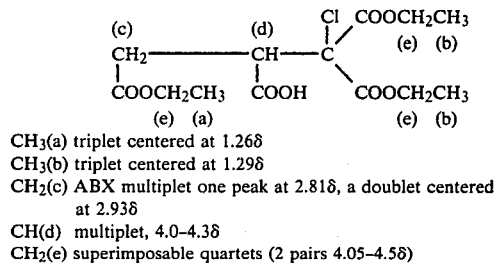

CH₃(a) triplet centered at 1.26δ
CH₃(b) triplet centered at 1.29δ
CH₂(c) ABX multiplet one peak at 2.81δ, a doublet centered at 2.93δ
CH(d) multiplet, 4.0–4.3δ
CH₂(e) superimposable quartets (2 pairs 4.05–4.5δ)

EXAMPLE XV

Preparation of Ethyl Hydrogen α-(Dimethyl Chloromalonyl)-Succinate

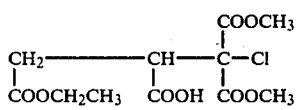

Seventy grams of the compound prepared in Example V, i.e. ethyl hydrogen α-(dimethylmalonyl)succinate is dissolved in 200 mls water. Five hundred grams of 5.2% sodium hypochlorite is then added slowly over a 30 minute period while maintaining the pH of the reaction mixture in the range 6-7 by the simultaneous addition of dilute hydrochloric acid. The reaction mixture is then acidified to a pH of 2 with concentrated hydrochloric acid and extracted with ethyl ether. After separation and evaporation of the ethyl ether layer, there is obtained 73 q (96.6% yield) of the title compound as a residue.

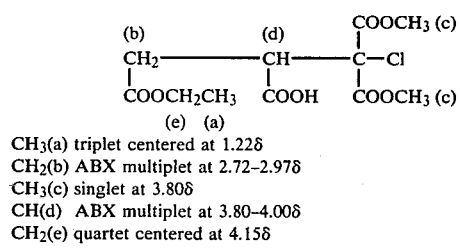

CH₃(a) triplet centered at 1.22δ
CH₂(b) ABX multiplet at 2.72–2.97δ
CH₃(c) singlet at 3.80δ
CH(d) ABX multiplet at 3.80–4.00δ
CH₂(e) quartet centered at 4.15δ

EXAMPLE XVI

Preparation of Methyl Hydrogen α-(Dimethyl Bromomalonyl)-Succinate

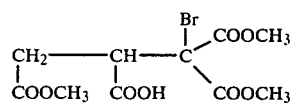

To 3.3 grams (0.0125 mol) of the compound of Example II, i.e. methyl hydrogen α-(dimethyl malonyl)succinate, dissolved in 100 mls water, is slowly added over a 15 minute period 27 mls of sodium hypobromite solution (4.2% by weight) to a pH of 7.0. After 20 minutes, the solution is acidified to a pH of 1.0 with dilute (5%) hydrochloric acid and extracted with ether. The ether extract is evaporated to give 3 g (75% yield) of the title compound as a syrupy residue. The structure is confirmed by NMR analysis (CDCl₃):

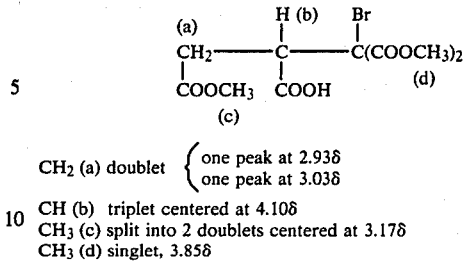

CH₂ (a) doublet { one peak at 2.93δ
                  one peak at 3.03δ
CH (b) triplet centered at 4.10δ
CH₃ (c) split into 2 doublets centered at 3.17δ
CH₃ (d) singlet, 3.85δ

EXAMPLE XVII

Preparation of Methyl Hydrogen α-(Dimethyl Hydroxymalonyl)-Succinate β-Lactone

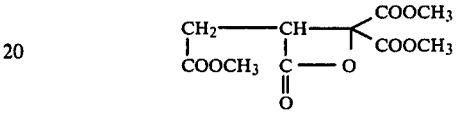

Twenty six grams of the compound prepared in Example II, i.e. methyl hydrogen α-(dimethyl malonyl)-succinate, is dissolved in 150 mls water. A solution of 5.25% sodium hypochlorite is then added slowly until the pH of the reaction mixture increases to 7.0. The water medium is then removed in vacuo at 40° C. to leave a yellow residue which is taken up in chloroform and filtered. The chloroform filtrate is evaporated to give a purified residue which is then redissolved in water and passed through a cation exchange resin in the acid form. The water layer in the eluate is separated and evaporated to give 25 grams of $$CH_2\text{------}CH\text{------}C\text{---}(COOCH_3)_2,$$
$$\hspace{0.8cm}|\hspace{1.4cm}|\hspace{1.4cm}|$$
$$\hspace{0.4cm}COOCH_3\hspace{0.3cm}COOH\hspace{0.3cm}Cl$$

as a residue. The organic layer (2 g) from the eluate corresponds to the lactone product (confirmed by infrared and NMR analysis). Infrared analysis shows a peak for a four membered lactone at 5.4β. The NMR analysis (CDCl₃) is as follows:

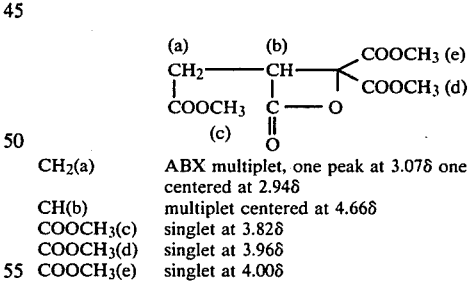

CH₂(a)  ABX multiplet, one peak at 3.07δ one doublet centered at 2.94δ
CH(b)   multiplet centered at 4.66δ
COOCH₃(c) singlet at 3.82δ
COOCH₃(d) singlet at 3.96δ
COOCH₃(e) singlet at 4.00δ

EXAMPLE XVIII

Preparation of Ethyl Hydrogen α-(Diethyl Hydroxymalonyl)-Succinate β-Lactone

Procedure A

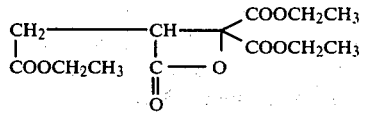

Ten grams (0.032 mole) of the compound prepared in Example XIV, i.e. ethyl hydrogen α-(diethyl chloromalonyl)-succinate is dissolved in 100 mls of ethanol and Ca(OH)₂ is added until the pH reaches 8.6. The ethanol is removed under vacuum at 45° C., 100 mls of pyridine is added and the resulting solution is heated at 90° C. for one hour. The pyridine is removed in vacuo and the residue is extracted with ethyl ether. Evaporation of the ether extracts gives 8 g (84% yield) of the title compound. The structure is confirmed by NMR analysis (CDCl₃):

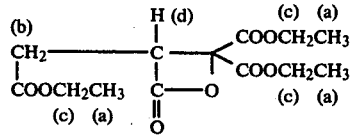

CH₃(a) superimposed triplets, 1.0–1.5δ
CH₂(b) ABX multiplet, 2.75–3.00δ
CH₂(c) superimposed quartets, 3.92–4.50δ
CH(d) ABX multiplet, 4.50–4.73δ

Procedure B

Six grams of the compound prepared in Example XIV, i.e. ethyl hydrogen α-(diethyl chloromalonyl)succinate, is dissolved in 50 mls of chloroform and 100 grams of triethyl amine is added. The solution is stirred at 40°–50° C. for 45 minutes. The excess amine and chloroform are removed in vacuo and the residue is extracted with ether. The ether extracts are then evaporated to dryness to give 5 grams of the title compound. The structure is confirmed by NMR analysis (CDCl₃).

EXAMPLE XIX

Preparation of Ethyl Hydrogen α-(Diethyl Hydroxymalonyl)-Succinate

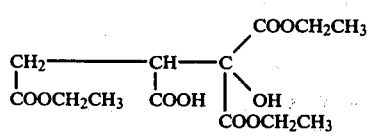

Five grams (0.016 mole) of the compound prepared in Example XIV, i.e. ethyl hydrogen α-(diethyl chloromalonyl)-succinate, is dissolved in 100 mls of water and Na₂CO₃ is added to a pH of 8.6. Sixty mls of pyridine is added and the solution is heated at 80° C. for one hour (at this point the pH is 7.0). The solvents (H₂O+- pyridine) are removed under vacuum and the residue is extracted with acetone. The acetone extract os evaporated to leave a residue of the sodium salt of the title compound. The structure is confirmed by NMR analysis (D₂O):

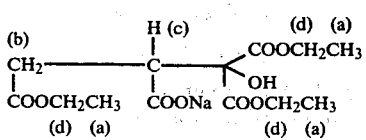

CH₃(a) superimposed triplets at 1.1–1.47δ
CH₂(b) ABX multiplet at 2.5–2.8δ
CH(c) ABX multiplet at 3.7–4.1δ
CH₂(d) superimposed quartets at 4.0–4.5δ

The above salt is dissolved in 100 mls of water and the pH is adjusted to 1.0 with dilute hydrochloric acid (10%). The acidified solution is then extracted with ethyl ether and the ether extract is evaporated to yield 3.5 g (70% yield) of the title compound. The structure is confirmed by NMR analysis (CDCl₃):

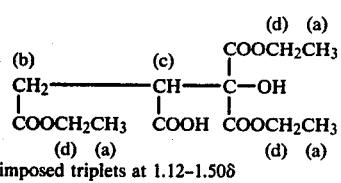

CH₃(a) superimposed triplets at 1.12–1.50δ
CH₂(b) ABX multiplet at 2.56–2.94δ
CH(c) ABX multiplet at 3.74–4.02δ
CH₂(d) superimposed quartets at 3.98–4.52δ

EXAMPLE XX

Preparation of Methyl Hydrogen α-(Dimethyl Hydroxymalonyl)-Succinate

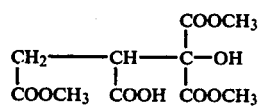

A mixture of 15 g (0.05 mole) of the compound prepared as in Example XII, i.e. methyl hydrogen α-(dimethyl chloromalonyl)succinate, and 200 ml of water is neutralized to a pH of 9.0 by the addition of 2.8 g (0.026 mole) of sodium carbonate. The resulting solution is refluxed for 30 minutes whereby the pH drops to about 2. The solution is evaporated and the residue extracted with acetone. The acetone solution is filtered and evaporated to yield 9 g of a syrupy product corresponding to the title compound. The structure is confirmed by NMR analysis (CDCl₃):

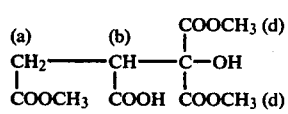

CH₂(a) ABX multiplet at 2.60–3.00δ
CH(b) hidden
CH₃(c) singlet at 3.76δ
CH₃(d) singlet at 3.90δ

EXAMPLE XXI

Preparation of α-(2-Hydroxy Disodium Malonyl)Disodium Succinate

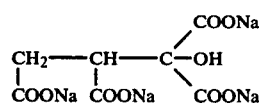

Ten grams (0.03 mole) of the compound prepared in Example XIV, i.e. ethyl hydrogen α-(diethyl chloromalonyl)-succinate is mixed with 75 ml water and 4.4 g (0.06 mole) of Ca(OH)₂. After 15 minutes an additional 3 grams of Ca(OH)₂ is added to maintain the pH at 9.5–10.0. The resulting mixture is heated at 60°–70° C. for 4 hours while stirring and maintaining the pH at 9.5–10.0 by further addition of Ca(OH)₂ as required. Sodium carbonate, 0.1 mole, is then added and the reaction mixture is stirred at 60°–70° C. for 15 minutes. The solution is filtered to remove CaCO₃ and the pH of the filtrate is adjusted to 9.0 with dilute hydrochloric acid.

After evaporation of the water, a residue of 9 g of the title compound containing traces of sodium chloride is obtained. The structure of the product is confirmed by NMR analysis (D₂O):

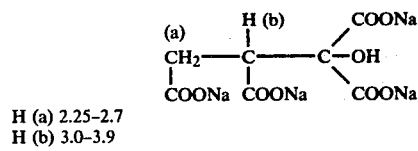

H (a) 2.25–2.7
H (b) 3.0–3.9

EXAMPLE XXII

Preparation of Isocitric and Alloisocitric Acid Lactones
Procedure A

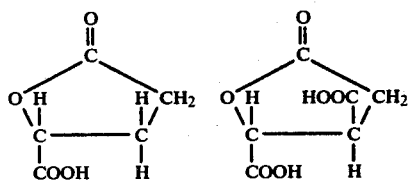

One gram of the product prepared in Example XXI above is acidified with dilute HCl (10% (with liberation of CO₂) and evaporated to dryness in vacuo. The product consists of a mixture of isocitric and alloisocitric acid lactones by NMR analysis (D₂O):

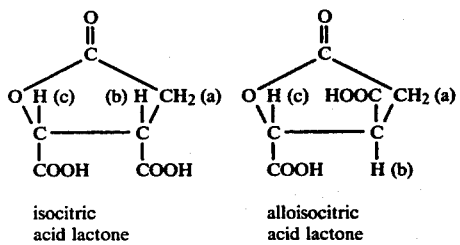

isocitric acid lactone      alloisocitric acid lactone

H (a) ABX multiplet at 2.94–3.28δ
H (b) ABX multiplet at 3.78–4.19δ
H (c) doublet at 5.38–5.58δ
H (c') doublet at 4.3–4.5δ (traces of isocitric acid and alloisocitric acid)

Procedure B

Fifty grams of the compound prepared in Example XIV, i.e. ethyl hydrogen α-(diethyl chloromalonyl)succinate is dissolved in 100 ml of water to which 10 ml of concentrated hydrochloric acid has been added. The solution is refluxed for 16 hours and then evaporated in vacuo to leave 28 g of a solid residue consisting of a 1:1 mixture of the lactones of isocitric acid and alloisocitric acid (structure determined by NMR analysis—D₂O).

EXAMPLE XXIII

Preparation of Tetrasodium Propene 1,1,2,3 Tetracarboxylate

Twelve grams (0.036 mole) of the product prepared in Example XII, i.e. methyl hydrogen α-(dimethyl chloromalonyl)succinate, is mixed with 200 mls water. Ca(OH)₂ is then slowly added at first maintaining the pH at 10.0 and then heating to 60°–70° C. until all the ester groups are saponified. A total of 10 grams of Ca(OH)₂ is added (pH 11.6) and the slurry is stirred for 2–3 hours at 60°–70° C. Thirteen grams of Na₂CO₃ is then added and the mixture is stirred for 15 minutes at 50° C. The precipitated CaCO₃ is filtered and the filtrate is evaporated to give 10 g of the title compound. The structure is confirmed by NMR analysis (D₂O): —CH₂— singlet at 3.34%.

EXAMPLE XXIV

Preparation of 1:1 Cis:Trans Aconitic Acid

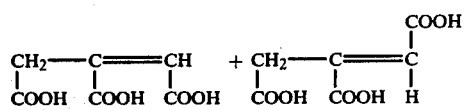

Nine grams of the product as prepared in Example XXIII, i.e. tetrasodium propane-1,1,2,3-tetracarboxylate, is dissolved in 100 mls water and acidified with dilute HCl (10%). Liberation of CO₂ is instantaneous. The residue, after evaporation of water, is extracted with acetone. The acetone is evaporated to leave a residue consisting of a 1:1 by weight mixture of cis:-trans aconitic acid. The structure of the product is confirmed by NMR analysis (D₂O):

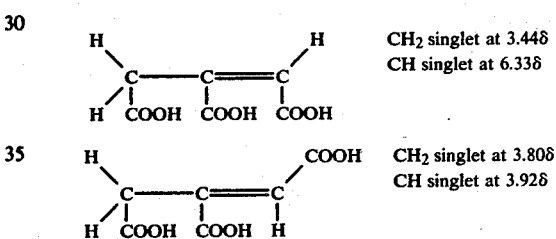

CH₂ singlet at 3.44δ
CH singlet at 6.33δ

CH₂ singlet at 3.80δ
CH singlet at 3.92δ

EXAMPLE XXV

Preparation of a Mixture of Isocitric Acid, Alloisocitric Acid and the Lactones Thereof Thirty grams (0.1 mole) of the compound prepared in Example XII, i.e. methyl hydrogen α-(dimethyl chloromalonyl)succinate, is mixed with 200 ml water. Sodium hydroxide, 20 g (0.5 mole), is added slowly while maintaining the temperature at 60° C. and the pH between 9 and 10. After heating for 3–4 hours at 60° C., the solution is cooled and acidified to a pH of 1.2 with dilute hydrochloric acid. The solution is then evaporated in vacuo and the residue remaining is extracted with acetone. The acetone extract is then filtered and the filtrate, evaporated to give a residue of 12 grams of mixture of 1:1 isocitric acid: alloisocitric acid and the lactones thereof (identified by NMR).

EXAMPLE XXVII

Preparation of a Mixture of Isocitric Acid, Alloisocitric Acid and the Lactones Thereof Fifteen grams (0.05 mole) of the product prepared in Example XV, i.e. ethyl hydrogen α-(dimethyl chloromalonyl)-succinate is mixed with 200 mls of water. Magnesium hydroxide, 25 g (0.43 mole), is added slowly while maintaining the reaction mixture at 80°–90° C. and the pH at 9.0. After refluxing the reaction mixture for 2 hours, the solution is cooled and then acidified with 86.2 g of 50% sulfuric acid. The acidified solution is evaporated to yield a residue which is then extracted with acetone. The acetone extract is filtered and the filtrate evaporated to give 10.4 of residue consisting of a mixture of isocitric acid and alloisocitric acid and the lactones thereof (identified by NMR).

EXAMPLE XXVIII

Preparation of a Mixture of Isocitric Acid, Alloisocitric Acid and the Lactones Thereof Fifteen grams (0.05 mole) of the compound prepared in Example XV, i.e. ethyl hydrogen α-(dimethyl chloromalonyl)-succinate, is mixed with 200 ml water. Strontium hydroxide, 24 g (0.2 mole), is then added while heating the mixture at 70°–75° C. and while maintaining the pH at 10.0. The solution is then cooled and acidified with 120 g of 15% hydrochloric acid. The acidified solution is then evaporated in vacuo to a residue which, in turn, is extracted with acetone. The acetone extract is filtered and the filtrate is evaporated in vacuo to given 7.7 grams of syrup consisting of a mixture of isocitric acid, alloisocitric acid and the lactones thereof (identified by NMR analysis).

This invention has been described with respect to certain preferred embodiments and various modifications and variations in the light thereof will be suggested to persons skilled in the art and are to be included within the spirit and preview of this application and the scope of the appended claims.

What is claimed is:

1. A propene 1,1,2,3-tetracarboxylate salt of the formula

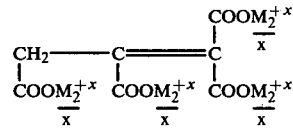

wherein $M_2$ is a lithium, sodium, potassium, calcium, strontium or barium cation and wherein x is 1 or 2 and is equivalent to the valency of $M_2$.

2. A compound as defined in claim 1 wherein $M_2$ is a sodium cation.

* * * * *

UNITED STATES PATENT AND TRADEMARK OFFICE
CERTIFICATE OF CORRECTION

PATENT NO. : 4,273,935
DATED : June 16, 1981
INVENTOR(S) : Eddie N. Gutierrez et al It is certified that error appears in the above—identified patent and that said Letters Patent is hereby corrected as shown below:

Column 13, line 56: Change "4-ethyl hydrogen α-(diethyl hydroxymalonyl)-succinate" to --sodium 4-ethyl hydrogen α-(diethyl hydroxymalonyl) succinate--.

Signed and Sealed this

Ninth Day of February 1982

[SEAL]

Attest:

GERALD J. MOSSINGHOFF

Attesting Officer

Commissioner of Patents and Trademarks